United States Patent
Guckenbiehl et al.

(10) Patent No.: US 6,428,776 B1
(45) Date of Patent: Aug. 6, 2002

(54) AQUEOUS COSMETIC PREPARATIONS IN STICK FORM

(75) Inventors: Bernhard Guckenbiehl; Bernhard Banowski, both of Duesseldorf; Holger Tesmann, Juechen, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/554,305

(22) PCT Filed: Oct. 30, 1998

(86) PCT No.: PCT/EP98/06896

§ 371 (c)(1),
(2), (4) Date: Oct. 11, 2000

(87) PCT Pub. No.: WO99/23866

PCT Pub. Date: May 20, 1999

(30) Foreign Application Priority Data

Nov. 11, 1997 (DE) .......................... 197 49 819

(51) Int. Cl.⁷ .............................................. A61K 7/32
(52) U.S. Cl. .......................................... 424/65; 424/401
(58) Field of Search .................... 424/401, 65

(56) References Cited

U.S. PATENT DOCUMENTS 5,980,874 A * 11/1999 Foerster et al. ............... 424/65

FOREIGN PATENT DOCUMENTS

| DE | 1 165 574 | 3/1964 |
| DE | 20 24 051 | 12/1971 |
| DE | 44 20 516 | 12/1995 |
| DE | 195 30 220 | 2/1997 |
| GB | 962 919 | 7/1964 |
| GB | 1 333 475 | 10/1973 |

OTHER PUBLICATIONS

*Surfactants in Consumer Products*, Springer Verlag, Berlin, 1987, pp. 54–124.
*Katalysatoren, Tenside* und Mineraloeladditive, Thieme Verlag, Stuttgart, 1978, pp. 123–217.
H. Tronnier, G. Rentschler, *Experimentelle Untersuchungen zur Wirkungsweise aluminiumhaltiger Antiperspiranzien*, J.Soc.Cosm. Chem. 24, 1973, p. 281.
A.B. Graham, M.V. Park, *Inhibition of the mitochondrial oxidation of octanoate by salicylic acid and related compounds*, J.Pharm. Pharmacol. 26, 1974 pp. 531–534.

* cited by examiner

Primary Examiner—Jose' G. Dees
Assistant Examiner—Konata M. George
(74) Attorney, Agent, or Firm—John E. Drach; Steven J. Trzaska

(57) ABSTRACT

A cosmetic composition containing: (a) an alkyl and/or alkenyl oligoglycoside corresponding to formula (I):

$$R^1O-[G]_p \qquad (I)$$

wherein $R^1$ is an alkyl and/or alkenyl radical having from 4 to 22 carbon atoms, G is a sugar radical having 5 or 6 carbon atoms, and p is a number from 1 to 10; (b) an oily compound; (c) a nonionic emulsifier; and (d) an active ingredient selected from the group consisting of an antiperspirant compound, a deodorant compound, an antibacterial active compound, and mixtures thereof, and wherein the composition is free of soap and natural wax.

12 Claims, No Drawings

AQUEOUS COSMETIC PREPARATIONS IN STICK FORM

BACKGROUND OF THE INVENTION

The invention relates to aqueous, soap- and wax-free cosmetic stick preparations comprising glucosides, oily substances and selected emulsifiers, and to the use of the mixtures for the preparation of deodorant sticks.

Water-containing cosmetic stick preparations which are to be found on the market as antiperspirant or deodorant products largely comprise soap (sodium stearate), oily substances and bactericides. They have an alkaline pH of about 9. The soapy feel on the skin associated with these sticks is regarded by the consumer as a disadvantage. A more recent development relates to sticks which comprise known antiperspirant active ingredients, such as, for example, aluminum chlorohydrate (ACH). They have to be formulated at an acidic pH of about 4 and for this require specific thickener systems, such as, for example, polydiols in combination with dibenzylidene sorbitol. In addition, for many years, there has been a large number of antiperspirant sticks based on natural or synthetic waxes on the market in which the active ingredient is incorporated as a powder into the wax matrix. The disadvantage here is that the sticks are very greasy, and a white residue often remains on the skin.

The complex object of the present invention was therefore to provide stick preparations which are free from the disadvantages described. In particular, the sticks were to be free from soaps so that acidic active ingredients can be incorporated, and also were not to contain waxes in order to avoid residues on the skin. At the same time, the sticks were to be notable for improved feel on the skin, high consistency and thermal resistance, and transparency or whiteness.

BRIEF SUMMARY OF THE INVENTION

The invention provides aqueous cosmetic preparations in stick form comprising
(a) alkyl and/or alkenyl oligoglycosides,
(b) oily substances and
(c) nonionic emulsifiers,
with the proviso that the preparations are free from soaps and natural waxes.

DETAILED DESCRIPTION OF THE INVENTION

Surprisingly, we have found that the preparations according to the invention not only exhibit sufficiently high consistency and thermal resistance, but also impart an advantageous feel to the skin. The preparations are soap-free and therefore permit the incorporation of acidic active ingredients, such as, for example, aluminum chlorohydrate. In this connection, the invention incorporates the knowledge that during the formulation it is possible to use not only active ingredient powders, but also aqueous solutions directly, which considerably simplifies the preparation and the homogeneous distribution within the stick. The sticks are transparent gels or pure white and do not leave behind any undesired residues upon application.

Alkyl and/or Alkenyl Oligoglycosides

Alkyl and alkenyl oligoglycosides are known nonionic surfactants which conform to the formula (I)

$$R^1O-[G]_p \qquad (I)$$

in which $R^1$ is an alkyl and/or alkenyl radical having from 8 to 22 carbon atoms, G is a sugar radical having 5 or 6 carbon atoms, and p is a number from 1 to 10. They can be obtained by the relevant processes of preparative organic chemistry, for example by acid-catalyzed acetalation of glucose with fatty alcohols.

The alkyl and/or alkenyl oligoglycosides can be derived from aldoses or ketoses having 5 or 6 carbon atoms, preferably glucose. The preferred alkyl and/or alkenyl oligoglycosides are therefore alkyl and/or alkenyl oligoglucosides. The index number p in the general formula (I) gives the degree of oligomerization (DP), i.e. the distribution of mono- and oligoglycosides, and is a number between 1 and 10. While p in a given compound must always be a whole number and here can assume in particular the values p=1 to 6, for a particular alkyl oligoglycoside, p is an analytically determined arithmetical value which is in most cases a fraction. Preference is given to using alkyl and/or alkenyl oligoglycosides having an average degree of oligomerization p of from 1.1 to 3.0. From an application viewpoint, preferred alkyl and/or alkenyl oligoglycosides are those whose degree of oligomerization is less than 1.7 and in particular between 1.2 and 1.4. The alkyl or alkenyl radical $R^1$ can be derived from primary alcohols having from 8 to 22, preferably from 12 to 16, carbon atoms. Typical examples are octanol, decanol, lauryl alcohol, myristyl alcohol, cetyl alcohol, palmoleyl alcohol, stearyl alcohol, isostearyl alcohol, oleyl alcohol, elaidyl alcohol, petroselinyl alcohol, arachidyl alcohol, gadoleyl alcohol, behenyl alcohol, erucyl alcohol, brassidyl alcohol, and technical-grade mixtures thereof, which can be obtained as described above. Preference is given to alkyl oligoglucosides based on lauryl and/or myristyl alcohol, and corresponding technical-grade coconut fatty alcohol cuts having a DP in the range from 1 to 3. The proportion of glucosides in the preparations can be from 1 to 40% by weight and, preferably, from 3 to 30% by weight.

Oily Substances

Suitable oily substances are, for example, Guerbet alcohols based on fatty alcohols having from 6 to 18, preferably from 8 to 10, carbon atoms, esters of linear $C_6$–$C_{22}$-fatty acids with linear $C_6$–$C_{22}$-fatty alcohols, esters of branched $C_6$–$C_{13}$-carboxylic acids with linear $C_6$–$C_{22}$-fatty alcohols, esters of linear $C_6$–$C_{22}$-fatty acids with branched alcohols, in particular 2-ethylhexanol, esters of linear and/or branched fatty acids with polyhydric alcohols (such as, for example, propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, esters of $C_2$–$C_{12}$-dicarboxylic acids with linear or branched alcohols having from 1 to 22 carbon atoms or polyols having from 2 to 10 carbon atoms and from 2 to 6 hydroxyl groups, vegetable oils, branched primary alcohols, substituted cyclohexanes, linear $C_6$–$C_{22}$-fatty alcohol carbonates, Guerbet carbonates, esters of benzoic acid with linear and/or branched $C_6$–$C_{22}$-alcohols (e.g. Finsolv® TN), dialkyl ethers, ring-opening products of epoxidized fatty acid esters with polyols, silicone oils and/or aliphatic or naphthenic hydrocarbons. The proportion of oily substances in the preparations can be from 1 to 50% by weight and, preferably, from 3 to 30% by weight.

Nonionic Emulsifiers

Suitable nonionic emulsifiers are, for example, nonionic surfactants from at least one of the following groups:
(c1) addition products of from 2 to 30 mol of ethylene oxide and/or from 0 to 5 mol of propylene oxide to linear fatty alcohols having from 8 to 22 carbon atoms, to fatty acids having from 12 to 22 carbon atoms and to alkylphenols having from 8 to 15 carbon atoms in the alkyl group;

(c2) $C_{12/18}$-fatty acid mono- and diesters of addition products of from 1 to 30 mol of ethylene oxide to glycerol;

(c3) glycerol mono- and diesters and sorbitan mono- and diesters of saturated and unsaturated fatty acids having from 6 to 22 carbon atoms and the ethylene oxide addition products thereof;

(c4) addition products of from 1 to 60 mol of ethylene oxide to castor oil and/or hydrogenated castor oil;

(c5) polyol and, in particular, polyglycerol esters, such as, for example, polyglycerol polyricinoleate or polyglycerol poly-12-hydroxystearate. Mixtures of compounds from two or more of these classes of substance are also suitable;

(c6) addition products of from 2 to 15 mol of ethylene oxide to castor oil and/or hydrogenated castor oil;

(c7) partial esters based on linear, branched, unsaturated or saturated $C_{12/22}$-fatty acids, ricinoleic acid, and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose);

(c8) mono-, di- and/or trialkyl phosphates;

(c9) wool wax alcohols;

(c10) polysiloxane-polyalkyl-polyether copolymers or corresponding derivatives;

(c11) mixed esters of pentaerythritol, fatty acids, citric acid and fatty alcohol as in German Patent 1165574 and/or mixed esters of fatty acids having from 6 to 22 carbon atoms, methylglucose and polyols, preferably glycerol, and (c12) polyalkylene glycols.

The addition products of ethylene oxide and/or of propylene oxide to fatty alcohols, fatty acids, alkylphenols, glycerol mono- and diesters, and sorbitan mono- and diesters of fatty acids or to castor oil are known, commercially available products. These are homologue mixtures whose average degree of alkoxylation corresponds to the ratio of the quantitative amounts of ethylene oxide and/or propylene oxide and substrate with which the addition reaction is carried out. $C_{12/18}$-fatty acid mono- and diesters of addition products of ethylene oxide to glycerol are known from German Patent 2024051 as refatting agents for cosmetic preparations. For the purposes of the invention, the use of polyglycerol poly-12-hydroxystearates and/or polyglycerol polyricinoleates as in DE-A1 4420516 (Henkel) is preferred since the oil-binding capacity of these emulsifiers is significantly superior to that of the customarily used glycerol monoricinoleates or of castor oil. The proportion of nonionic emulsifiers in the preparations can be from 1 to 30% by weight and, preferably, from 3 to 10% by weight. Preference is given to using lipophilic emulsifiers having HLB values below 10.

Coemulsifiers

Suitable coemulsifiers are anionic and/or amphoteric or zwitterionic surfactants. Typical examples of anionic surfactants are soaps, alkylbenzenesulfonates, alkanesulfonates, olefinsulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular vegetable products based on wheat) and alkyl (ether) phosphates. If the anionic surfactants contain polyglycol ether chains, these can have a conventional homologue distribution, but preferably have a narrowed homologue distribution. Typical examples of amphoteric or zwitterionic surfactants are alkylbetaines, alkylamidobetaines, aminopropionates, aminoglycinates, imidazoliniumbetaines and sulfobetaines. Said surfactants are exclusively known compounds. With regard to structure and preparation of these substances, reference may be made to relevant reviews, for example J. Falbe (ed.), "*Surfactants in Consumer Products*", Springer Verlag, Berlin, 1987, pp. 54–124 or J. Falbe (ed.), "Katalysatoren, Tenside und Mineralöladditive" [*Catalysts, Surfactants and Mineral Oil Additives*], Thieme Verlag, Stuttgart, 1978, pp. 123–217. The proportion of coemulsifiers in the preparations can be from 0 to 30% by weight, and preferably, from 1 to 15% by weight.

Bodying Agents

As additional component having coemulsifying properties, the preparations can further comprise bodying agents, for example of the fatty alcohol type. This term is to be understood as including primary aliphatic alcohols of the formula (II)

$$R^2OH \qquad (II)$$

in which $R^2$ is an aliphatic, linear or branched hydrocarbon radical having from 6 to 22 carbon atoms and 0 and/or 1, 2 or 3 double bonds. Typical examples are caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaostearyl alcohol, arachidyl alcohol, gadoleyl alcohol, behenyl alcohol, erucyl alcohol and brassidyl alcohol, and technical-grade mixtures thereof which are formed, for example, during the high-pressure hydrogenation of technical-grade methyl esters based on fats and oils or aldehydes from the Roelen oxo synthesis, and as monomer fraction during the dimerization of unsaturated fatty alcohols. Preference is given to technical-grade fatty alcohols having from 12 to 18 carbon atoms, such as, for example, coconut fatty alcohol. The proportion of fatty alcohols in the preparations can be from 1 to 35% by weight and, preferably, from 5 to 30% by weight.

Alternatively, diols can also be used as bodying agents. Typical examples thereof are 1,12-dodecanediol, 1,16-hexadecanediol, 12-hydroxystearyl alcohol, and ring-opening products of epoxidized $C_6$–$C_{22}$-olefins with water or polyols, preferably glycerol. The proportion of diols in the preparations can be from 1 to 35% by weight and, preferably, from 5 to 30% by weight.

Fatty acid partial glycerides can also be used as a further group of bodying agents, i.e. monoglycerides, diglycerides and technical-grade mixtures thereof which, depending on the preparation, can still contain small amounts of triglycerides. The partial glycerides preferably conform to the formula (III)

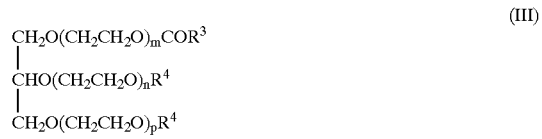

in which $R^3CO$ is a linear or branched, saturated or unsaturated acyl radical having from 6 to 22, preferably from 12 to 18, carbon atoms, $R^4$ and $R^5$ independently of one another are $R^1CO$ or OH, and the sum (m+n+p) is 0 or a number from 1 to 100, preferably from 5 to 25, with the proviso that at least one of the two radicals $R^4$ and $R^5$ is OH. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaostearic acid, arachidic acid, gadoleic acid, behenic acid and erucic acid, and technical-grade mixtures thereof. Preference is given to using technical-grade lauric glycerides, palmitic glycerides, stearic glycerides, isostearic glycerides, oleic glycerides, behenic glycerides and/or erucic glycerides which have a monoglyceride content in the range from 50 to 95% by weight, preferably from 60 to 90% by weight. The proportion of fatty acid partial glycerides in the preparations can be from 1 to 35% by weight and, preferably, from 5 to 30% by weight.

Active Ingredients

Suitable antiperspirants are, for example, aluminum chlorohydrates. These are colorless, hygroscopic crystals which readily deliquesce in air and produce aluminum chloride solutions upon evaporation. Aluminum chlorohydrate is used for the preparation of antiperspirant and deodorizing preparations and probably acts via the partial closure of the sweat glands by protein and/or polysaccharide precipitation [cf. *J. Soc. Cosm. Chem.* 24, 281 (1973)]. For example, an aluminum chlorohydrate is available commercially under the trade name Locron® from Hoechst AG, Frankfurt/FRG, which corresponds to the formula $[Al_2(OH)_5Cl]*2.5\ H_2O$ and whose use is particularly preferred [cf. *J. Pharm. Pharmacol.* 26, 531 (1975)]. As well as the chlorohydrates, it is also possible to use aluminum hydroxylactates and acidic aluminum/zirconium salts. Other deodorant active ingredients which may be added are esterase inhibitors. These are preferably trialkyl citrates, such as trimethyl citrate, tripropyl citrate, triisopropyl citrate, tributyl citrate and, in particular, triethyl citrate (Hydagen® CAT, Henkel KGaA, Dusseldorf/FRG). The substances inhibit the enzyme activity, thus reducing the formation of odor. Presumably, in this process, the cleavage of the citric ester results in the release of the free acid, which lowers the pH on the skin sufficiently for the enzymes to be inhibited. Other substances which are suitable as esterase inhibitors are dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate. Antibacterial active ingredients, which influence the bacterial flora and destroy bacteria which decompose perspiration or inhibit them in their growth, can likewise be present in the stick preparations. Examples thereof are chitosan, phenoxyethanol and chlorhexidine gluconate. 5-Chloro-2-(2,4-dichlorophenoxy) phenol, which is sold under the trade name Irgasan® by Ciba-Geigy, Basel/CH, has proven particularly effective. The proportion of active ingredients in the preparations can be from 0 to 30% by weight and, preferably, from 0.1 to 15% by weight.

Silicone Compounds

Suitable silicone compounds are, for example, dimethylpolysiloxanes, methylphenylpolysiloxanes, cyclic silicones, and amino-, fatty-acid-, alcohol-, polyether-, epoxy-, fluoro-, glucoside- and/or alkyl-modified silicone compounds which, at room temperature, can either be liquid or in the form of a resin. The proportion of silicone compounds in the preparations can be from 0 to 20% by weight and, preferably, from 1 to 10% by weight.

Industrial Applicability

In a preferred embodiment of the invention, the cosmetic preparations have the following compositions:

(a) from 1 to 40% by weight, preferably from 3 to 30% by weight, of alkyl and/or alkenyl oligoglycosides, (b) from 10 to 50% by weight, preferably from 15 to 35% by weight, of oily substances, (c) from 1 to 30% by weight, preferably from 3 to 10% by weight, of nonionic emulsifiers, (d) from 0 to 35% by weight, preferably from 1 to 15% by weight, of coemulsifiers, (e) from 0 to 35% by weight, preferably from 5 to 30% by weight, of bodying agents, (f) from 0 to 30% by weight, preferably from 1 to 15% by weight, of active ingredients, (g) from 0 to 20% by weight, preferably from 1 to 10% by weight, of silicone compounds, and (h) from 0 to 20% by weight, preferably from 5 to 10% by weight, of lower alcohols, with the proviso that the figures are made up to 100% by weight with water and optionally other customary auxiliaries and additives. The water content in the preparations can be from 10 to 70% by weight and, preferably, from 25 to 50% by weight.

Other auxiliaries and additives which may be present in the preparations according to the invention are superfatting agents, such as, for example, lanolin and lecithin, and polyethoxylated or acylated lanolin and lecithin derivatives, polyol fatty acid esters, monoglycerides and fatty acid alkanolamides. As well as water, solvents which may be used are lower alcohols, preferably ethanol, and polyols, such as, for example, propylene glycol, glycerol, polyglycerol and the like, in amounts up to 25% by weight. Stabilizers which may be used are metal salts of fatty acids, such as, for example, magnesium, aluminum and/or zinc stearate. Examples of suitable biogenic active ingredients are bisabolol, allantoin, phytantriol, panthenol, AHA acids, tocopherols, plant extracts and vitamin complexes. Preservatives which may be used are parabens or phenoxyethanol, optionally in the mixture with ethanol. Dyes which may be used are the substances permitted and suitable for cosmetic purposes, as listed, for example, in the publication "Kosmetische Färbemittel" [Cosmetic Colorants] from the Farbstoffkommission der Deutschen Forschungs-gemeinschaft [Dyes Commission of the German Research Society], Verlag Chemie, Weinheim, 1984, pp. 81–106. These dyes are customarily used in concentrations of from 0.001 to 0.1% by weight, based on the total mixture. The total content of auxiliaries and additives can be from 1 to 5% by weight, preferably from 2 to 4% by weight, based on the compositions.

The invention further provides for the use of aqueous mixtures comprising (a) alkyl and/or alkenyl oligoglycosides, (b) oily substances and (c) nonionic emulsifiers for the preparation of deodorant sticks.

EXAMPLES

Examples 1 to 9

The components according to Table 1 were melted together at about 80° C. and stirred until homogeneous. The mixture was then poured into a prewarmed stick mold. The application properties were determined subjectively as follows:

|  | +++ | ++ | + |
|---|---|---|---|
| Consistency | soft, but stable | medium | hard |
| Thermal resistance | stable at 50° C. | begins to soften at 50° C. | semi-liquid at 50° C. |
| Care | slightly greasy | greasy | soapy |

The results are given in Table 1.

TABLE 1

Compositions and properties of deodorant sticks (quantitative data as % by weight)

| Composition | 1 | 2 | 3 | 4 | 5 | 6 | 7 | 8 | 9 |
|---|---|---|---|---|---|---|---|---|---|
| Coco glucosides | 13.5 | 19.6 | 6.6 | 8.6 | 13.5 | 6.6 | 5.5 | 3.2 | 8.5 |
| Glyceryl oleate | 20.6 | 15.0 | — | — | — | — | — | — | — |
| Glyceryl stearate | — | — | 34.0 | 23.0 | 20.6 | 21.0 | 32.0 | 18.9 | 13.0 |
| Diisooctyl-cyclohexane | 13.4 | 2.0 | 13.4 | 13.4 | 13.4 | — | 13.4 | 5.9 | 8.5 |
| Dimethicone | — | — | — | — | — | — | — | 2.0 | — |
| Octyldodecanol | — | — | — | — | — | 13.4 | — | — | — |
| Aluminum chlorohydrate | 20.0 | 20.0 | 20.0 | 20.0 | 20.0 | 20.0 | 20.0 | 20.0 | 20.0 |
| Triethyl citrate | — | — | — | — | 2.0 | 2.0 | — | — | — |
| Chitosan | — | — | — | — | — | 1.0 | — | 10.0 | 10.0 |
| Ethanol | — | — | — | — | — | — | — | — | 10.0 |
| Water | ad 100 | | | | | | | | |
| Application properties | | | | | | | | | |
| Consistency | +++ | +++ | ++ | ++ | ++ | ++ | ++ | +++ | +++ |
| Thermal resistance | ++ | ++ | +++ | ++ | ++ | ++ | +++ | ++ | ++ |
| Care | +++ | +++ | +++ | ++ | ++ | ++ | +++ | +++ | +++ |

What is claimed is:

1. A cosmetic composition comprising:
   (a) an alkyl and/or alkenyl oligoglycoside corresponding to formula (I):

$$R^1O\text{---}[G]_p \tag{I}$$

wherein $R^1$ is an alkyl and/or alkenyl radical having from 4 to 22 carbon atoms, G is a sugar radical having 5 or 6 carbon atoms, and p is a number from 1 to 10;
   (b) an oily compound;
   (c) a nonionic emulsifier; and
   (d) an active ingredient selected from the group consisting of an anti-perspirant compound, a deodorant compound, an antibacterial active compound, and mixtures thereof, and wherein the composition is free of soap and natural wax.

2. The composition of claim 1 wherein the alkyl and/or alkenyl oligoglycoside is present in the composition in an amount of from 1 to 40% by weight, based on the weight of the composition.

3. The composition of claim 1 wherein the oily compound is present in the composition in an amount of from 1 to 50% by weight, based on the weight of the composition.

4. The composition of claim 1 wherein the nonionic emulsifier is present in the composition in an amount of from 1 to 30% by weight, based on the weight of the composition.

5. The composition of claim 1 wherein the active ingredient is present in the composition in an amount of from 0.1 to 15% by weight, based on the weight of the composition.

6. The composition of claim 1 wherein the composition is in a solid, stick form.

7. A process for inhibiting formation of perspiration and/or odor on human skin comprising contacting the skin with a composition containing:
   (a) an alkyl and/or alkenyl oligoglycoside corresponding to formula (I):

$$R^1O\text{---}[G]_p \tag{I}$$

wherein $R^1$ is an alkyl and/or alkenyl radical having from 4 to 22 carbon atoms, G is a sugar radical having 5 or 6 carbon atoms, and p is a number from 1 to 10;
   (b) an oily compound;
   (c) a nonionic emulsifier; and
   (d) an active ingredient selected from the group consisting of an anti-perspirant compound, a deodorant compound, an antibacterial active compound, and mixtures thereof, and wherein the composition is free of soap and natural wax.

8. The process of claim 7 wherein the alkyl and/or alkenyl oligoglycoside is present in the composition in an amount of from 1 to 40% by weight, based on the weight of the composition.

9. The process of claim 7 wherein the oily compound is present in the composition in an amount of from 1 to 50% by weight, based on the weight of the composition.

10. The process of claim 7 wherein the nonionic emulsifier is present in the composition in an amount of from 1 to 30% by weight, based on the weight of the composition.

11. The process of claim 7 wherein the active ingredient is present in the composition in an amount of from 0.1 to 15% by weight, based on the weight of the composition.

12. The process of claim 7 wherein the composition is in a solid, stick form.

* * * * *